United States Patent [19]

Murthy et al.

[11] 4,306,944
[45] Dec. 22, 1981

[54] CYCLOHEXANONE DISTILLATION PROCESS

[75] Inventors: Andiappan K. Murthy, Lake Hiawatha; David Y. Hsieh, Florham Park, both of N.J.

[73] Assignee: Allied Corporation, Morris Township, Morris County, N.J.

[21] Appl. No.: 165,905

[22] Filed: Jul. 3, 1980

[51] Int. Cl.³ .............................................. B01D 3/14
[52] U.S. Cl. ....................................... 203/77; 203/80; 203/DIG. 19; 568/366
[58] Field of Search ............... 568/366; 203/71, 73, 203/77, 80, 91, DIG. 19

[56] References Cited
U.S. PATENT DOCUMENTS
4,158,611  6/1979  Cooke ........................ 203/DIG. 19

OTHER PUBLICATIONS
"Chemical Engineer's Handbook", Perry; 4th ed; 1963.

*Primary Examiner*—Frank Sever
*Attorney, Agent, or Firm*—Alan M. Doernberg; Gerhard H. Fuchs

[57] ABSTRACT

An improved process of distilling a cyclohexanone-rich overhead stream in a first still from a feed mixture comprising cyclohexanone, phenol and cyclohexanol of the type wherein a cyclohexanone-rich stream is withdrawn as a part of an overheads condensate from the first still and a phenol-rich stream is withdrawn as a part of a reboiled bottom stream from the first still. The improvement includes withdrawing a side stream substantially free of phenol from above the point where the feed mixture is fed to the first column and separating the side stream in a second still into a second cyclohexanone-rich overhead stream and a bottom stream containing cyclohexanone and cyclohexanol. The second cyclohexanone-rich stream may be returned to the first still.

7 Claims, 3 Drawing Figures

CYCLOHEXANONE DISTILLATION PROCESS

BACKGROUND OF THE INVENTION

The present invention relates to the separation of cyclohexanone from mixtures thereof with cyclohexanol and phenol such as are formed by the selective hydrogenation of phenol. It is conventional to subject such mixtures to three successive fractional distillations with the first overheads stream recovered being a cyclohexanone-rich stream containing cyclohexanol at a level between 0.1 and 0.5 percent, the second overheads stream being a mixture of cyclohexanone and cyclohexanol between 50 and 80 percent cyclohexanone and the third overheads stream being a phenol-rich steam containing significant amounts of cyclohexanol and cyclohexanone. Certain high boilers such as cyclohexylcyclohexanone remain in the bottoms in all three distillations and are removed from the system at the bottom of the third column.

Because cyclohexanone is produced in large quantities by hydrogenation of phenol for uses such as caprolactam manufacture, and because such distillations consume substantial amounts of steam or other heat energy for reboiling and require substantial amounts of cooling water for condensing, the possibility of modifying such distillation so as to produce more cyclohexanone for the same steam and cooling water consumption would be a desirable result. Similarly, because such distillations require large and expensive equipment, an increase in the capacity of a series of stills to produce more cyclohexanone would also be desirable. Furthermore, there are many uses for cyclohexanone in which it is desirable to achieve lower levels of cyclohexanol content, while in other uses significantly higher cyclohexanol contents can be tolerated.

BRIEF DESCRIPTION OF THE INVENTION

The present invention includes a process of distilling a cyclohexanone-rich overheads stream in a first still from a feed mixture comprising cyclohexanone, phenol and cyclohexanol of the type wherein a cyclohexanone-rich stream is withdrawn as a part of an overheads condensate from a first still and a phenol-rich stream is withdrawn as part of a reboiled bottoms stream from the first still. According to the invention, a side stream substantially free of phenol is withdrawn from above the point where the feed mixture is fed to the first column and the side stream is distilled in a second column into a second cyclohexanone-rich overheads stream and a reboiled bottoms stream comprising cyclohexanone and cyclohexanol.

Operating according to the present invention permits the same amount of equipment to distill more feed mixture using less reboiler energy and less condensation energy than conventional systems. Furthermore, cyclohexanone of higher quality can be formed in the second column or, alternatively, energy can be saved by forming a cyclohexanone of lower quality from the second column. As a third alternative, the cyclohexanone-rich overheads stream of the second still can be established at a greater cyclohexanol level than the desired product, and this overheads can be returned to the first still above the point where the side stream is withdrawn.

DETAILED DESCRIPTION OF THE INVENTION

Figure 1:
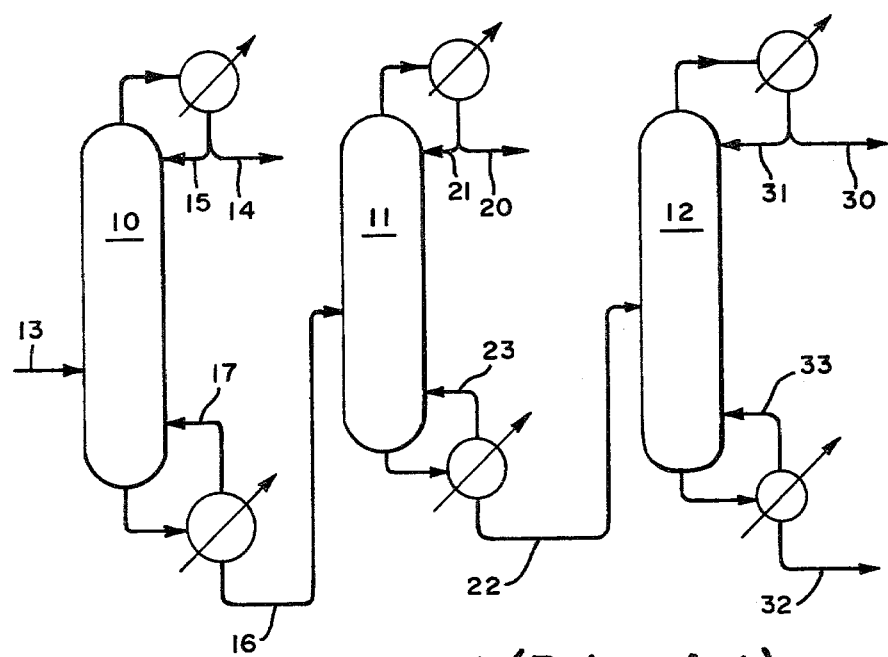
FIG. 1 is a schematic view of a prior art process.

The present invention is applicable to feed mixtures having phenol contents ranging from very small amounts (i.e. 1 percent) up to about 50 percent of the feed. Feed mixtures having more cyclohexanone than cyclohexanol are preferred, with the ratio of cyclohexanone to cyclohexanol being at least about 1, preferably at least about 5, more preferably at least about 10 and most preferably at least about 20. Materials other than phenol, cyclohexanone and cyclohexanol may also be present, and in particular water and high boilers such as cyclohexylcyclohexanone and cyclohexylcyclohexanol may be present in minor amounts such as 1 percent or less of a feed mixture. All proportions will be given herein by mol percent, with the understanding that weight percentages will be essentially equivalent at least among phenol, cyclohexanol and cyclohexanone based upon their close molecular weights.

The feed mixture is fed to the first column at an intermediate point, preferably below the midpoint of the column. It will be understood that, based upon variations in column efficiency, column configuration, reflux ratio and reboil ratio, the feed point is subject to being moved. It is desirable for the present invention that sufficient theoretical plates of distillation be present below the feed point and a sufficiently high reboil ratio be used so that the bottoms stream which is preferably withdrawn from the reboiler contain the minimum amounts of cyclohexanone and cyclohexanol reasonably achievable. Unlike conventional distillations wherein it is desired to withdrawn cyclohexanone, cyclohexanol and phenol in the first bottoms stream, it is the intention of the present invention to withdraw phenol and high boilers quantitatively in the first bottoms stream and to withdraw only a minimum of cyclohexanone and cyclohexanol. Thus the phenol rich stream withdrawn from the first still has about 30 to 40 mol % combined cyclohexanone and cyclohexanol.

Above the feed point, it is desirable to have sufficient numbers of theoretical plates to first condense all of the phenol from the vapor and second, above the point where all of the phenol is removed to have a significant number of plates wherein cyclohexanone is separated from cyclohexanol. It will be appreciated that, in the absence of phenol, cyclohexanone is more volatile than cyclohexanol. By contrast, when the phenol concentration is more than 30%, cyclohexanol appears more volatile than cyclohexanone. The number of such theoretical plates above the feed point and above the level where the mixture is substantially free of phenol will depend on the reflux ratio chosen as well as on the withdrawal of a side stream as described below and upon whether or not a second overhead stream is returned to the first column as described below.

A feature of the present invention is that a side stream is withdrawn from the first column above the feed point at a level where the phenol content is negligible. The side stream may either be of vapor or of liquid, but is preferably of liquid because smaller volumes will then result in more material being withdrawn and because, at such point, the liquid phase is likely to contain a higher cyclohexanol proportion than is the vapor phase.

This side stream is then fed to a second fractional distillation column at an intermediate point. Because the cyclohexanol-cyclohexanone system behaves in a relatively ideal manner compared to phenol-cyclohexanone and phenol-cyclohexanol, the operation of the second still is relatively conventional, with the feed point, reflux ratio and reboil ratio chosen in conventional fashion to achieve the desired high proportion of cyclohexanone and low proportion of cyclohexanol in the overheads. It will be appreciated that the side stream may be split into one or more streams which are then fed to one or more second stills which may each be designed to produce a cyclohexanone-rich overhead stream of the same quality or, alternatively, to produce cyclohexanone-rich streams of different qualities. One or more of these cyclohexanone-rich streams may be of the same quality as the overheads stream from the first column. Alternatively, one or more of these overheads streams may have cyclohexanol contents substantially higher than the cyclohexanol content of the overhead stream from the first column. In the latter case, the overheads from such a second column may be fed back to the first column at a point above the point where the side stream is withdrawn, but below the point where overheads are withdrawn and reflux is returned to the first column. Preferably, such overhead stream from the second column is returned as a liquid at a point in the first column where the liquid phase has substantially the same cyclohexanol content as does the material being returned.

The bottoms from the first column, containing phenol, high boilers and some cyclohexanol and cyclohexanone may then be distilled in a conventional fashion to produce an overhead stream of phenol, cyclohexanol and cyclohexanone which can be recirculated to the hydrogenation reaction. The bottoms from the third column may be reformed, reused in some other manner, or used as boiler fuel.

The operation of the present invention will be made clear by reference to the figures.

FIG. 1 shows a prior art scheme for operation of a first still 10, a second still 11 and a third still 12 for continuously distilling cyclohexanone, a cyclohexanone-cyclohexanol stream and a phenol-rich stream from a feed mixture containing cyclohexanone, phenol, cyclohexanol and high boilers. Briefly, the feed mixture is fed in stream 13 to the first still 10 with the overheads condensed and then partitioned between a cyclohexanone-rich product stream 14 and a first reflux stream 15. The bottoms of the first still 10 are withdrawn and reboiled and then partitioned into a first forward bottoms stream 16 and a first return stream 17. The feed point, reflux ratio and reboil ratio are together selected in a manner to produce a first product stream 14 rich in cyclohexanone and having essentially no phenol or high boilers and having a desired maximum permissible cyclohexanol content which is typically between 0.1 and 0.5 percent.

The first bottoms forward stream 16 is then fed to an intermediate point in the second column 11 where it is distilled and the overheads are condensed and partitioned between a second product stream 20 and a second reflux stream 21 and the bottoms are withdrawn and heated and partitioned between a second bottoms forward stream 22 and a reboil return stream 23. The feed point, reflux ratio and reboil ratio of the second column are designed to remove as much as possible of the cyclohexanol and cyclohexanone from the bottoms forward stream 16 as second product stream 20. It will be appreciated that product stream 20 may be used for purposes such as adipic acid manufacture whereas any cyclohexanol or cyclohexanone present in forward stream 22 is likely to be subjected to further hydrogenation with the resultant build up of cyclohexanol in the system.

The second bottoms forward stream 22 is then fed to an intermediate point of a third still 12 with the overheads condensed and partitioned between a third product stream 30 and a reflux stream 31 and the bottoms heated and partitioned between a high boiler-rich stream 32 and a reboiler return stream 33. The feed point, reflux ratio and reboil ratio are designed to recover essentially all of the phenol, cyclohexanone and cyclohexanol from second bottoms forward stream 22 in third product stream 30 with essentially none of these materials remaining in high boiler-rich stream 32. Conventionally, third product stream 30 is then recycled to a hydrogenation system so that the phenol present therein may be converted to the desired cyclohexanone product. At least some of the cyclohexanone in third product stream 30 and all of the cyclohexanol content of stream 30 will result in additional cyclohexanol being removed from the hydrogenation reactor into feed stream 13 and thus increase the load upon the first two columns.

Figure 2:
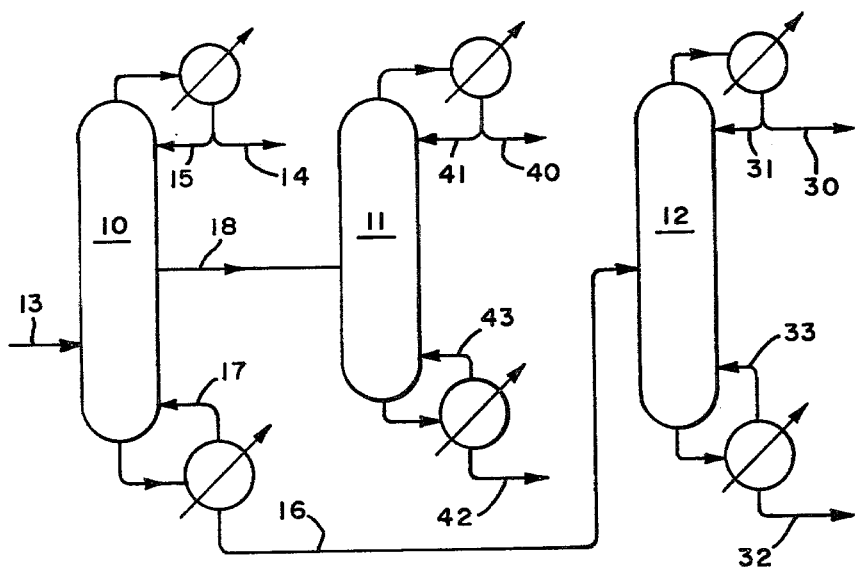
FIG. 2 is a schematic view of a process according to a first embodiment of the present invention.

FIG. 2 shows one distillation scheme according to the present invention. As in FIG. 1, a feed mixture is fed in stream 13 to the first column 10 and the overheads are condensed and partitioned into first product stream 14 and reflux stream 15, while the bottoms are withdrawn, heated and partitioned into a first bottoms forward stream 16 and a reboil return stream 17. In addition, however, a side stream 18 is withdrawn from the first column from a point above the feed point of stream 13 and below the return point of first reflux stream 15. The reboil ratio, reflux ratio, feed point of stream 13 and withdrawal point of stream 18 are together chosen in a manner that will simultaneously achieve several objectives. First, it is an objective that reboil forward stream 16 contain as little cyclohexanone and cyclohexanol as can be practically achievable. One method of achieving this objective is to employ a relatively large reboil ratio (defined as the flow rate in stream 17 divided by the flow rate in stream 16). Reboil ratios of greater than 10 are typical. The second objective is for sufficient theoretical plates of distillation to be present above the feed point of stream 13 to first strip all of the phenol and high boilers and then second strip cyclohexanol down to the purity level desired in first product stream 14. The withdrawal of side stream 18, however, causes the amount of material to be stripped of cyclohexanol to be materially reduced such that, with the same reflux ratio, it is, in general, possible to achieve lower cyclohexanol proportion in stream 14 than in the convenional system of FIG. 1. Alternatively, it is possible to use a somewhat lower reflux ratio and achieve the same quality of cyclohexanone in stream 14. The bottoms forward stream 16 is fed to the third column 12 which can then operate in the same manner as third column 12 in the prior art system of FIG. 1, producing a phenol-rich overheads stream 30 and a high boiler-rich bottoms stream 32 with, preferably, essentially all of the phenol, cyclohexanone and cyclohexanol fed to the column 12 in stream 16 being removed from the column in stream 30.

The side stream 18 from the first column 10, preferably being a liquid stream substantially free of high boilers and phenol but containing significantly more cyclohexanol than first overhead stream 14 is then fed to the second column 11. Second column 11 then operates in the fashion of a simple still to separate two materials which behave essentially in accordance with Raoult's law. Based upon the size, configuration and efficiency of still 11, the reflux ratio (reflux stream 41 divided by third product stream 40) and the reboil ratio (reboil return stream 43 divided by bottoms forward stream 42), the desired level of separation can be achieved. As depicted in FIG. 2, a single still 11 may be used to produce an overhead stream 40 which contains cyclohexanone of the desired low cyclohexanol content, which may be the same or different compared to the cyclohexanone quality of first product stream 14. The remainder of the material from stream 18 is removed in stream 42 and contains an appreciably larger cyclohexanol content than did stream 18. In general, the content of stream 42 in the novel scheme of FIG. 2 will be similar to the content of stream 20 in FIG. 1, and may be used for like purposes as, for example, in the production of adipic acid.

It is contemplated within the present invention to use one or more such second stills 11 which may produce cyclohexanone-rich overhead streams 40 having the same or different cyclohexanol contents. Such overhead streams 40 may then be used for different purposes depending upon tolerance for cyclohexanol for each such different purpose. Furthermore, it is contemplated in situations where the capacity of the first still 10 above the withdrawal of stream 18 is greater than the capacity of the available second stills 11 that some or all of the second product streams 40 will be returned to still 10 at a point above the withdrawal of side stream 18 and with or below the return of reflux stream 15, preferably at a point where the liquid in first still 10 is of substantially the same relative proportions of cyclohexanone and cyclohexanol as the material being returned.

Figure 3:
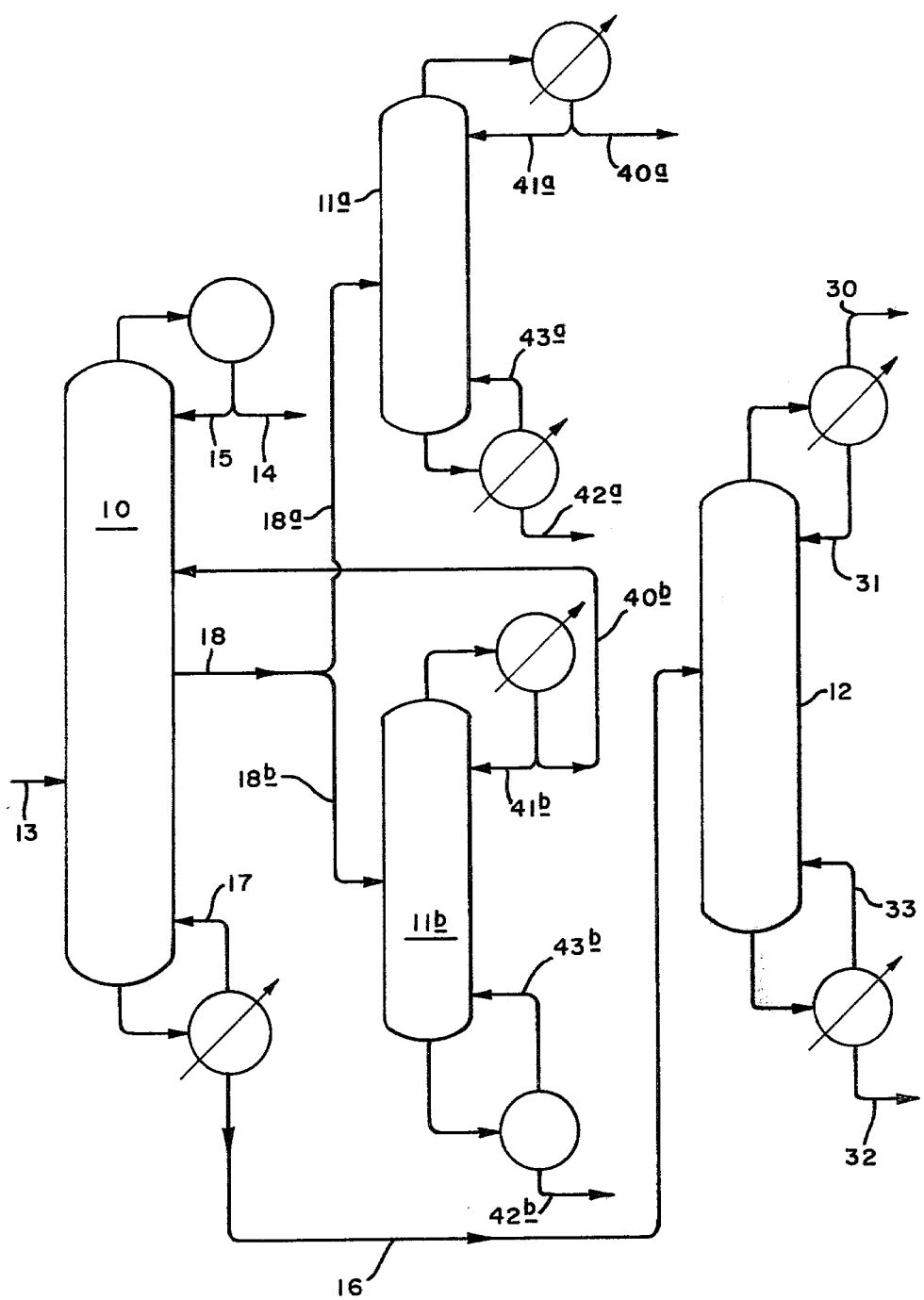
FIG. 3 is a schematic view of a process according to a second embodiment of the present invention.

FIG. 3 shows a distillation system similar to that of FIG. 2 except that the sidestream 18 from the first still 10 is split into two feeds 18a and 18b to two second stills 11a and 11b. Still 11a operates like still 11 produces a cyclohexanone-rich overhead 40a (with reflux 41a) and a cyclohexanol-rich bottoms 42a (with return 43a). Still 11b operates similarly except that it is expected to produce an overhead stream 40b rich in cyclohexanone, but having a higher cyclohexanol content than streams 14 or 40a. This stream 40b is returned to still 10 at a point above the withdrawal of sidestream 18 and below the return of reflux 15. The point of return is chosen to approximately match the liquid phase in column 10 with the cyclohexanone to cyclohexanol ratio in stream 40b.

COMPARATIVE EXAMPLE

The system of FIG. 1 is operated using an 80 tray first still 10 with stream 13 fed to the 35th tray from the bottom at the temperature and proportions (in mols per hour) shown in Table 1. The condenser of the first still is operated at a pressure of 70 torr (9.33 kPa), a vapor flux of 6 mol/h-cm² and a reflux ratio (stream 15 divided by stream 14) of 3.25. The heat withdrawn at the condenser is 6819 kcal/h. The reboiler of still 10 operates at a pressure of 362 torr (48.3 kPa) and a reboil ratio (stream 17 divided by stream 16) of 9.5. Stream 17 is returned to the first tray from the bottom. The heat supplied at the reboiler is 5005 kcal/h. The average Murphee stage efficiency of the column is 60% and the pressure drop of each tray is about 3.6 torr (0.48 kPa). The amounts and compositions withdrawn through streams 14 and 16 are as indicated in Table 1. Stream 16 is fed to the 30th tray of a 60-tray still 11 whose condenser is operated at 70 torr (9.33 kPa) pressure, 4 mol/h-cm² vapor flux and 1491 kcal/h heat removed and a 3.00 reflux ratio, and whose reboiler is operated at 375 torr (50 kPa) and 1444 kcal/h heat added and an 8.0 reboil ratio. Products withdrawn through streams 20 and 22 are as indicated in Table 1.

TABLE 1

| | CONVENTIONAL DISTILLATION (FIG. 1) | | | | |
|---|---|---|---|---|---|
| Stream | 13 (feed) | 14 (ohd) | 16 (btm) | 20 (ohd) | 22 (btm) |
| Cyclohexanone | 187.97 | 154.53 | 33.44 | 33.09 | 0.35 |
| Cyclohexanol | 8.08 | 0.47 | 7.61 | 2.91 | 4.70 |
| Phenol | 10.63 | 0.00 | 10.63 | 0.00 | 10.63 |
| High boilers | 0.70 | 0.00 | 0.70 | 0.00 | 0.70 |
| Total | 207.38 | 155 | 52.38 | 36.00 | 16.38 |
| Temperature | 120° C. | 82° C. | 139° C. | 83° C. | 160° C. |

EXAMPLE 1

The comparative example is repeated feeding the same feed stream 13 to the 12th tray of still 10 as shown in FIG. 2. The condenser of still 10 is operated at a 3.65 reflux ratio with 4862 kcal/h withdrawn; the reboiler of still 10 is operated at a 17.1 reboil ratio with 3118 kcal/h supplied. The pressures (70 and 362 torr), vapor flux (6 mol/h-cm²) and efficiency (60%) are as in the comparative example.

Overhead stream 14, bottoms stream 16 and sidestream 18 (at the 40th tray) are withdrawn from still 10 with proportions (in mol/h) as shown in Table 2. Stream 18 is fed to the 20th tray of a 60-tray still 11 whose condenser is operated at a reflux ratio of 4.25 with 2938 kcal/h withdrawn and whose reboiler is operated at a reboil ratio of 8.0 with 1444 kcal/h supplied. The pressures (70 and 375 torr), vapor flux (4 mol/h-cm²) and efficiency (60%) are as in the comparative example. Overheads stream 40 and bottoms stream 42 are withdrawn at the composition and rate (in mol/h) indicated in Table 2.

TABLE 2

| | NOVEL DISTILLATION WITHOUT RETURN (FIG 2) | | | | | |
|---|---|---|---|---|---|---|
| Stream | 13 (feed) | 14 (ohd) | 16 (btm) | 18 (sdstrm) | 40 (ohd) | 42 (btm) |
| Cyclohexanone | 187.97 | 100.70 | 4.76 | 82.51 | 53.84 | 28.67 |
| Cyclohexanol | 8.08 | 0.30 | 0.29 | 7.49 | 0.16 | 7.33 |
| Phenol | 10.63 | 0.00 | 10.63 | 0.00 | 0.00 | 0.00 |
| High boilers | 0.70 | 0.00 | 0.70 | 0.00 | 0.00 | 0.00 |
| Total | 270.38 | 101.00 | 16.38 | 90.00 | 54.00 | 36.00 |
| Temperature | 120° C. | 82° C. | 161° C. | 114° C. | 82° C. | 131° C. |

EXAMPLE 2

The comparative example is repeated using the stills 10 and 11b of FIG. 3 feeding the same feed mixture in stream 13 to the twelfth tray of column 10. The condenser of column 10 is operated at a reflux ratio of 2.85 with 6177 kcal/h withdrawn, and the reboiler of column 10 is operated at a reboil ratio of 24.4 with 4434 kcal/h supplied. The pressures (70 and 362 torr), vapor flux (6 mol/h-cm$^2$) and efficiency (60%) are as in the comparative example. Overheads stream 14, bottoms stream 16 and sidestream 18 (at the 40th tray) are withdrawn from still 10 at the compositions and rates indicated in Table 3, with sidestream 18 fed to the 45th tray of second still 11b.

TABLE 3
NOVEL DISTILLATION WITH RETURN
(FIG 3 WITHOUT STILL 11a)

| Stream | 13 (feed) | 14 (ohd) | 16 (btm) | 18 (sdstrm) | 40b (ohd) | 42b (btm) |
|---|---|---|---|---|---|---|
| Cyclohexanone | 187.97 | 154.41 | 4.62 | 81.80 | 53.07 | 28.73 |
| Cyclohexanol | 8.08 | 0.49 | 0.43 | 8.20 | 0.93 | 7.27 |
| Phenol | 10.63 | 0.00 | 10.63 | 0.00 | 0.00 | 0.00 |
| High boilers | 0.70 | 0.00 | 0.70 | 0.00 | 0.00 | 0.00 |
| Total | 207.38 | 155.00 | 16.38 | 90.00 | 54.00 | 36.00 |
| Temperature | 120° C. | 82° C. | 161° C. | 114° C. | 82° C. | 131° C. |

The condenser of second still 11b is operated at a reflux ratio of 2.30 withdrawing 1847 kcal/h; and the reboiler of second still 11b is operated at a reboil ratio of 5.2 with 1799 kcal/h supplied. The pressures (70 and 375 torr), vapor flux (4 mol/h-cm$^2$) and efficiency (60%) are as in the comparative example. Overheads stream 40b and bottoms stream 42b are withdrawn at the rates and compositions (in mol/h) shown in Table 3, with overheads stream 40b returned to the 70th tray of first still 10.

RESULTS

A comparison of the cyclohexanone overheads streams (14 in Table 1, 14 and 40 in Table 2 and 14 in Table 3) indicates that the same quantity and quality of cyclohexanone is produced in each case. The loads of the condensers, in kcal/h, are as follows:

|  | First Still | Second Still | Total |
|---|---|---|---|
| Comparative Example | 6819 | 1491 | 8310 |
| Example 1 | 4862 | 2938 | 7800 |
| Example 2 | 6177 | 1847 | 8024 | such that 6% and 3% savings in cooling water are achieved.

The loads on the reboilers, in kcal/h, are as follows:

|  | First Still | Second Still | Total |
|---|---|---|---|
| Comparative Example | 5005 | 1444 | 6449 |
| Example 1 | 3118 | 2891 | 6009 |
| Example 2 | 4434 | 1799 | 6233 | such that 6.8% and 3.3% reductions in heat input (e.g. steam consumption) are achieved.

More significantly, a higher proportion of the total cyclohexanol fed to the first column is removed in the stream containing cyclohexanol and cyclohexanone (stream 20 in FIG. 1; stream 42 in FIG. 2 and stream 42b in FIG. 3). Of the 8.08 mols per hour fed in through stream 13, the proportion removed and proportion still present with the phenol after distillation are:

|  | Cyclohexanol-Cyclohexanone Stream | | Phenol-rich Recycle | |
|---|---|---|---|---|
|  | Stream | Cyclohexanol | Stream | Cyclohexanol |
| Comparative Example | 20 | 2.91 | 22 | 4.70 |
| Example 1 | 42 | 7.33 | 16 | 0.29 |
| Example 2 | 42b | 7.27 | 16 | 0.43 |

The remainder of the 8.08 mols per hour of cyclohexanol is present as a minor impurity in the cyclohexanone-rich overheads (streams 14, 40 and 40b).

Since the phenol-rich stream is recycled to the hydrogenation reactor, after distillation from high boilers in the third column, less cyclohexanol will be recycled to the hydrogenation reactor in the process of the present invention than in the prior art process of the Comparative Example. This will cause the cyclohexanol content of the effluent from the reactor to decline, enabling the distillation columns to operate at lower reflux and reboil ratios to produce the same quality of cyclohexanone-rich overheads. Eventually, a steady state condition will be reached wherein the cyclohexanol content of the effluent remains constant, but this steady state condition will enable more effluent to be distilled in the same columns (because of the lowered reflux and reboil ratios). Thereby the energy and capital costs per unit product can be reduced.

The present invention is not limited, however, to the embodiments illustrated and described, but includes modifications, deletions and additions within the spirit and essential characteristics of the invention as indicated by the claims that follow.

What is claimed is:

1. In a process of distilling a cyclohexanone-rich overhead stream in a first still from a feed mixture comprising cyclohexanone, phenol and cyclohexanol of the type wherein a cyclohexanone-rich stream is withdrawn as a part of an overheads condensate from the first still and a phenol-rich stream is withdrawn as a part of a reboiled bottom stream from the first still, the improvement further comprising withdrawing a side stream substantially free of phenol from above the point where the feed mixture is fed to the first column and separating the side stream in a second still into a second cyclohexanone-rich overhead stream and a bottom stream containing cyclohexanone and cyclohexanol.

2. The process of claim 1 wherein the second cyclohexanone-rich stream is returned to the first still above the point where the side stream is withdrawn.

3. The process of claim 2 wherein the second cyclohexanone-rich stream is returned to a point in the first still having substantially the same proportion of cyclohexanone and cyclohexanol as the second cyclohexanone-rich stream being returned.

4. The process of claim 1 or 2 or 3 wherein the side stream is a liquid stream.

5. The process of claim 1 wherein the side stream is split into at least two streams fed to at least two second stills.

6. The process of claim 5 wherein at least one second cyclohexanone-rich stream from at least one second still is returned to the first still above the point where the side stream is withdrawn.

7. The process of claim 1 wherein the phenol-rich stream withdrawn from the first still has about 30 to 40 mol % combined cyclohexanone and cyclohexanol.

* * * * *